US00PP30540P3

(12) United States Plant Patent
Gerdts et al.

(10) Patent No.: US PP30,540 P3
(45) Date of Patent: May 28, 2019

(54) NECTARINE TREE NAMED 'BURNECTTHIRTYTHREE'

(50) Latin Name: *Prunus persica nucipersica*
Varietal Denomination: Burnectthirtythree

(71) Applicant: WAWONA PACKING CO., LLC, Cutler, CA (US)

(72) Inventors: Timothy J. Gerdts, Kingsburg, CA (US); John K. Slaughter, Fresno, CA (US)

(73) Assignee: Wawaona Packing Co., LLC, Cutler, CA (US)

( * ) Notice: Subject to any disclaimer, the term of this patent is extended or adjusted under 35 U.S.C. 154(b) by 3 days.

(21) Appl. No.: 15/731,044

(22) Filed: Apr. 11, 2017

(65) Prior Publication Data

US 2018/0295761 P1 Oct. 11, 2018

(51) Int. Cl.
*A01H 5/08* (2018.01)
*A01H 6/74* (2018.01)

(52) U.S. Cl.
USPC ..... Plt./190
CPC ..... *A01H 6/7454* (2018.05)

(58) Field of Classification Search
USPC ..... Plt./190
See application file for complete search history.

*Primary Examiner* — Keith O. Robinson
(74) *Attorney, Agent, or Firm* — Potter Anderson and Corroon, LLP

(57) ABSTRACT

A new and distinct variety of nectarine tree which is denominated varietally as 'Burnectthirtythree', and which produces an attractively colored yellow-fleshed, clingstone nectarine which is mature for harvesting and shipment approximately July 30 to August 5 under the ecological conditions prevailing in the San Joaquin Valley of central California.

1 Drawing Sheet

Botanical designation: *Prunus persica nucipersica.*
Varietal denomination: 'Burnectthirtythree'.

BACKGROUND OF THE NEW VARIETY

The present variety of nectarine tree resulted from an on-going program of fruit and nut tree breeding. The purpose of this program is to improve the commercial quality of deciduous fruit and nut varieties, and rootstocks, by creating and releasing promising selections of *Prunus, Malus, Punica* and *Juglans* species. To this end we make both controlled and hybrid cross pollinations each year in order to produce seedling populations from which improved progenies are evaluated and selected.

The seedling, 'Burnectthirtythree' was originated by us, and selected from a population of seedlings growing in our experimental orchards which are located near Fowler, Calif. The seedlings, grown on their own roots, were derived from planting seed of an open pollinated seedling which was identified as, 'J10.067', (unpatented), and which further produces a white-fleshed, sub-acid, clingstone nectarine. The pollen parent of this open pollinated seedling is unknown. The resulting fruit was collected from the female parent ('J10.067') at a mature stage, and then seeds were extracted in June of 2005. After a period of stratification, the seed was placed in the greenhouse, by population, and then field planted for tree establishment, and ultimately to exhibit fruit for evaluation. One nectarine seedling which produced yellow-fleshed fruit, and which further is the present variety, exhibited especially desirable characteristics, and was then designated as 'N53.015'. This seedling was marked for subsequent observation. After the 2008 fruiting season, the new variety of nectarine tree was selected for advanced evaluation, and repropagation.

ASEXUAL REPRODUCTION

Asexual reproduction of this new and distinct variety of nectarine tree was accomplished by budding the new nectarine tree onto 30 trees which had previously been established with 'Nemaguard' Rootstock (un-patented). This was performed by us in our employer's experimental orchard which is located near Fowler, Calif. Subsequent evaluations of these asexually reproduced plants have shown those asexual reproductions run true to the original tree. All characteristics of the original tree, and its fruit, were established, and appear to be transmitted through these succeeding asexual propagations.

SUMMARY OF VARIETY

'Burnectthirtythree' is a new and distinct variety of nectarine tree, which is considered of relatively large size, and which further has a vigorous growth characteristic. This new tree is also a regular, and productive bearer of relatively large, firm, yellow-fleshed and acidic clingstone fruit which have a very good flavor, and eating qualities. This new nectarine tree has a medium chilling requirement of approximately 600 hours, and further produces relatively uniformly sized fruit throughout the tree's canopy. In addition to the foregoing, the fruit of the new nectarine also appears to have good handling and shipping qualities. The 'Burnectthirtythree' Nectarine tree also bears fruit which are typically ripe for commercial harvesting and shipment on approximately July 30 to August 5 under the ecological conditions prevailing in the San Joaquin Valley of central California. In relative comparison to the 'August Red' nectarine tree (U.S. Pat. No. 6,363), which is the closest known variety, the current variety of nectarine tree bears fruit that ripen approximately 1 week before the harvesting date of the 'August Red' nectarine tree. Further, the current variety, in addition to ripening before the harvesting date of the fruit of the 'August Red' Nectarine tree, produces fruit which are about 4.0-6.0 millimeters larger. This earlier fruit ripening of the new variety, before the 'August Red' comparator, allows the fruit of the new variety to reach the marketplace before the fruit produced by the 'August Red' variety. Additionally, the current variety of Nectarine tree exhibits a 'showy flower' while the 'August Red' variety exhibits a 'non-showy flower' type. In relative comparison to the unpatented seed parent 'J10.067', the current variety is easily and clearly distinguishable because it produces fruit having a yellow flesh, whereas the seed parent produces fruit having a white flesh characteristic. Moreover, the current variety of nectarine tree has an acidic flesh, whereas the seed parent has flesh having low malic acid levels.

BRIEF DESCRIPTION OF THE DRAWINGS

The accompanying drawing, which is provided, is a color photograph of two whole mature fruit harvested from a tree which is five years old and which further displays both the apical and lateral aspects thereof. One mature fruit is seen, and which is bisected transversely through the sagittal plane, and which further reveals the flesh color, and stone characteristics thereof. The external coloration of the fruit as shown in the supplied photograph is sufficiently matured for harvesting and shipment. The colors in the photograph, as provided, are as nearly true as is reasonably possible in a color representation of this type. Due to chemical development, processing, and printing, the fruit depicted in this photograph may, or may not, be accurate when compared to the actual specimen. For this reason, future color references should be made to the color plates (Royal Horticultural Society, Fourth Edition, 2001), and descriptions provided, hereinafter.

NOT A COMMERCIAL WARRANTY

The following detailed description has been prepared to solely comply with the provisions of 35 U.S.C. § 112, and does not constitute a commercial warranty, (either expressed or implied), that the present variety will, in the future, display all the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological and botanical details of this new and distinct variety of nectarine tree, the following has been observed during the tenth fruiting season, and under the ecological conditions prevailing at the orchards of the assignee which are located near the town of Fowler, county of Fresno, state of Calif. All major color code designations are by reference to The R.H.S. Colour Chart (Royal Horticultural Society, Fourth Edition, 2001) provided by The Royal Horticultural Society of Great Britain. Common color names are also occasionally used.

Tree:

*Size*.—Generally the tree is considered medium, to medium-large in its growth pattern, as compared to other common commercial nectarine cultivars ripening in the late season of maturity. The tree of the present variety was pruned to a height of approximately 270.0 cm. to about 310.0 cm., at commercial maturity.

*Crown width*.—Approximately 285.0 cm.

*Vigor*.—Considered moderately vigorous. The present nectarine tree variety grew from about 175.0 cm. to about 180.0 cm., in height, during the first growing season. The new variety was pruned to a height of approximately 150.0 cm. during the first dormant season, and primary scaffolds were then selected for the desired tree structure.

*Productivity*.—Productive. Fruit set varies from a desired crop load, to levels higher than desired amounts, when the new variety is grown in a suitable horticultural zone, and under appropriate commercial nursery conditions. The fruit set is spaced by thinning to develop the remaining fruit into the desired market-sized fruit. The number of the fruit set varies with the prevailing climatic conditions, and the cultural practices employed.

*Fruit bearing*.—Regular. Fruit set has been more than adequate during the previous years of observation, and thinning was necessary during the past 10 years on both the original seedling and on subsequent asexually reproduced trees.

*Tree form*.—Upright, and pruned into a vase shape.

*Density*.—Considered moderately dense. It has been discovered that pruning the branches from the center of the tree to obtain a resulting vase shape allows for enhanced air movement, and appropriate amounts of sunlight to improve fruit color, and renewal of fruiting wood throughout the tree.

*Hardiness*.—The present tree was grown and evaluated in USDA Hardiness Zone 9. The calculated winter chilling requirements of the new tree is approximately 650 hours at a temperature below 7.0 degrees C. The present variety appears to be hardy under typical central San Joaquin Valley climatic conditions.

Trunk:

*Diameter*.—Approximately 17.0 cm in diameter when measured at a distance of approximately 15.24 cm. above the soil level. This measurement was taken at the end of the 7th growing season.

*Bark texture*.—Considered moderately rough, with folds of papery scarfskin being present. Since bark development, and coloration change with advancing tree age, this characteristic varies with the tree vigor, tree age and regional conditions. Therefore, this is not a dependable descriptor of the new variety.

*Lenticels*.—Numerous flat, oval lenticels are present. The lenticels range in size from approximately 5.0 millimeters to about 7.0 mm. in width, and between about 1.0 and about 2.0 millimeters in height. The development and size of the trunk lenticels can be influenced, to some degree, by the ambient growing conditions, and are not, necessarily, a dependable characteristic of this variety. As trees of this variety mature, lenticels are present, but they are generally covered by increasing layers of cork, (mature bark), and therefore become less apparent.

*Lenticel color*.—Considered an orange brown, (RHS Greyed-Orange Group 164 B).

*Bark coloration*.—Variable, but it is generally considered to be a greyed brown, (RHS Grey-Green Group 197 B). This bark description was taken from trees in their sixth leaf which have ruptured the scarf skin, and which also have developed bark furrowing which is much more typical of the bark of older trees. It should be noted that the coloration of the bark is influenced, and varies, as the smoother, darker background color approaches other bark features such as the lenticels, and the initial fissures which form a feature of the scarf skin development.

Branches:

*Size*.—Considered medium-large for the variety.

*Diameter*.—Average as compared to other nectarine varieties. The branches have a diameter of about 11.0 centimeters when measured during the 6th year after grafting.

*Flowering shoot thickness*.—At bloom, shoot thickness can vary from approximately 4.0 mm to more than 8.0 mm.

*Surface texture*.—Average, and appearing relatively smooth but with more furrowing on wood which is several years old.

*Crotch angles*.—Primary branches are considered variable, and are usually growing at an angle of about 46 to about 50 degrees when measured from a horizontal plane. This particular characteristic can vary due to the influence of the assorted ecological conditions, and the cultural practices which are being utilized.

*Current season shoots*.—Surface texture — Substantially glabrous.

*Internode length*.—Approximately 2.4 cm.

*Color of mature branches*.—Approximately Grey-brown, (RHS Greyed-Orange Group 177 C).

*Current season's shoots*.—Color. — Light green, (RHS Yellow-Green Group 145 C). The color of new shoot tips is considered a bright and shiny green (RHS Yellow-Green Group 146 D). The vegetative shoot color can be significantly influenced by plant nutrition, irrigation practices, and exposure to sunlight, and therefore should not be considered a consistent botanical characteristic of this new variety.

Leaves:

*Size*.—Considered somewhat elongated, and narrow for the species. Leaf measurements have been taken from vigorous, upright, current-season growth, at approximately mid-shoot. It should be understood that the leaf size is often influenced by prevailing growing conditions, quality of sunlight, and the location of the leaf within the tree canopy. For this reason, leaf sizes can vary significantly based upon the ambient, and other cultural factors listed above, and are not typically considered a dependable botanical descriptor.

*Leaf length*.—Approximately 148.0 to about 155.0 millimeters.

*Leaf width*.—Approximately 30.0 to about 33.0 millimeters.

*Leaf base-shape*.—The leaves generally exhibit equal marginal symmetry relative to the leaf longitudinal axis.

*Leaf form*.—Lanceolate.

*Leaf tip form*.—Acuminate.

*Leaf color*.—Upper Leaf Surface — Medium green, (approximately RHS Green Group 137 A).

*Leaf texture*.—Upper Leaf Surface — Glabrous. Lower Leaf Surface — Glabrous.

*Leaf color*.—Lower Leaf Surface — Medium-green, (approximately RHS Green Group 146 B).

*Leaf venation*.—Pinnately veined.

*Mid-vein*.—Color — Considered a light yellow, (approximately RHS Greyed-Yellow Group 160 C) in the early to mid-period of the growing season.

*Leaf margins*.—Gently undulating. Form. — Considered finely crenate. Uniformity. — Considered generally uniform.

*Leaf petioles*.—Form. — Considered canaliculated, and having a more pronounced trough when viewed from the dorsal aspect. The petiole margin is considered rounded when viewed from the ventral aspect. Size. — Considered medium-small for the species. Length. — About 8.0 to about 11.0 mm. Diameter. — About 1.5 to about 2.0 mm. Color. — A light yellow green, (approximately RHS Yellow-Green Group 145 A). Strength. — Durable for the species until senescence.

*Leaf glands*.—Size. — Considered relatively small for the species; approximately 2.0 mm. in length; and about 1.0 mm. in height. Number. — Generally, one, and less commonly two glands appear per marginal side. Observations of more than two glands per marginal side are very uncommon. Type. — Glands located at the base of the leaf are predominantly reniform in shape. An additional one to two, or occasionally more glands, which appear reniform, and stalked, are often present and can be found at the basal margin of the leaf petiole as well. Color. — Considered a medium-dark brown, approximately (RHS Brown Group 199 A). Typically, the coloration of the glands darkens, and occasionally begins to desiccate during the mid-late growing season.

*Leaf stipules*.—Size. — Typically, the stipule is approximately 12.0 mm to 20.0 mm in length and approximately 2.0 mm in width. Number. — Typically 2 per leaf bud, and up to 6 per shoot tip. Form. — Lanceolate in form, and having a serrated marginal edge. Color. — Green, (approximately RHS Green Group 137 B) when young, but graduating to a brown color, (approximately RHS Greyed-Orange Group 165 A) with advancing senescence. The leaf stipules are generally considered to be early deciduous.

Flower buds:

*Hardiness*.—No winter injury (bud death) has been noted during the last several years of observation in the central San Joaquin Valley. The new variety of nectarine tree has not been intentionally subjected to drought, cold or heat stress, and therefore this information is not available.

*Flower bud*.—Size — Variable, and dependent upon the state of maturity. The flower buds, as described, were observed approximately 7 days prior to bloom. Flower Bud Length — Approximately 15.5 millimeters. Flower Bud Diameter — Approximately 8.5 millimeters. Flower Bud Surface Texture. — Pubescent. Flower Bud Orientation. — Considered appressed, but appear less so as the blossoms near opening.

*Bud scale color*.—Approximately RHS Greyed-Orange Group 175 A.

Flowers:

*Date of first bloom*.—Observed on Feb. 24, 2016, the blooming time is considered average in relative comparison to other commercial nectarine cultivars grown in the central San Joaquin Valley. The date of full bloom was observed on Mar. 2, 2016. The date of full bloom varies slightly with climatic conditions, and prevailing cultural practices.

*Duration of bloom*.—Approximately 8 or more days. This particular characteristic varies slightly with the prevailing climatic conditions.

*Flower class*.—Considered a perfect flower, complete and perigynous.

*Flower type*.—The variety is considered to have a showy-type flower.

*Flower size*.—Considered large for the species. The flower diameter, at full bloom, is approximately 57.0 to 60.0 millimeters.

*Bloom quantity*.—Considered abundant.

*Flower bud density*.—Generally considered dense.

*Flower bud frequency*.—Generally two flower buds appear per node, occasionally one flower bud per node is observed. Very rarely three floral buds per node are observed.

*Petal size*.—Generally considered medium-large for the species. Petal Length. — Approximately 26.0 to 28.0 millimeters. Petal Width. — Approximately 21.0 to 26.0 millimeters.

*Petal form*.—Considered broadly ovate.

*Petal count*.—Nearly always 5.

*Petal texture*.—Upper Petal Texture. — Very finely pubescent, and satin like. Lower Petal Texture. — Very finely pubescent, satin like.

*Petal color*.—Considered a light pink at the popcorn stage, (RHS Red-Purple Group 65 B), and darkening, with advanced senescence, and the exposure of sunlight, to a medium-dark pink, (RHS Red-Purple 63 C). This darkening of the petal color is generally most present within the margins of the petal claw.

*Fragrance*.—Slight.

*Petal claw*.—Form. — The claw is considered ovate, and is generally large. Length. — Approximately 14.0 to 16.0 millimeters. Width. — Approximately 10.5 to 14.0 millimeters.

*Petal margins*.—Generally it is moderately undulate, and ruffled, especially apically.

*Petal apex*.—Often the petal margin exhibits a shallow, and wide recess at the tip.

*Petal width*.—Approximately 2.5 to 4.0 millimeters.

*Petal depth*.—1.0 to 2.0 millimeters.

*Flower pedicel*.—Length. — Considered medium-long with an approximate length of about 1.5 to about 3.5 millimeters. Diameter. — Approximately 2.5 millimeters. Color. — A medium-brown, approximately (RHS Grey-Brown Group N199 D), depending on the pedicel and fruit maturity, and the timing of the visual observance. Strength. — Tenacious. Average for the species. Texture. — Generally smooth, to slightly undulate.

*Floral nectaries*.—Color. — Considered a dull brown (approximately RHS Greyed-Orange Group 175 B).

*Calyx*.—Surface Texture. — Generally glabrous. Color. — A dull grey purple, (approximately RHS Greyed-Purple Group 185 B).

*Sepals*.—Number. — 5. Size. — Medium large. Sepal Length. — Approximately 5.0 to 8.0 millimeters. Sepal Width. — Approximately 4.0 to 6.0 millimeters. Sepal Shape. — Generally obovate. Sepal Margin. — Considered smooth and entire. Sepal Color. — A dull grey-purple, (approximately RHS Greyed-Green Group 197 B).

*Anthers*.—Generally, — Average in size, having a width of approximately 2.0 mm, a length of approximately 2.0 mm, and a depth of approximately 1.0 mm. Color. — Yellow, when viewed dorsally, and prior to dehiscence, (approximately RHS Greyed-Yellow Group 162 B). Position Relative to the Stigma. — Generally the stigma is superior to the anthers by approx. 1.0-2.0 millimeters at the time of pollen dehiscing and dispersal.

*Pollen production*.—Pollen is abundant, and has a yellow color, (approximately RHS Yellow-Orange Group 18 A).

*Fertility*.—Self-fertile.

*Filaments*.—Size. — Approximately 17.5 to 20.0 millimeters in length. Color. — Considered white, (RHS Red Yellow Group 11 D).

*Pistil*.—Number. — Usually one, and only rarely more than one. Generally. — Large in size. Length. — Approximately 19.0 to about 22.0 millimeters in length, including the ovary. Ovary — Glabrous. Color. — Considered a very pale green, (approximately RHS Yellow-Green Group 154 D). Surface Texture. — The variety has a long, glabrous pistil. Position Relative to the Petals. — At flower maturity the stamens grow to be superior to the petals.

Fruit:

*Maturity when described*.—Firm ripe condition (shipping ripe).

*Date of first picking*.—Approximately Jul. 30, 2016.

*Date of last picking*.—Aug. 12, 2016. The date of harvest can vary, somewhat, with the prevailing climatic conditions, volume of fruit on the tree, and the current climatic and cultural practices employed.

*Size*.—Generally — Considered medium-large.

*Average cheek diameter*.—Approximately 76.0 to about 80.0 millimeters.

*Average axial diameter*.—Approximately 74.0 to about 79.0 millimeters.

*Typical weight*.—Approximately 225.0 grams. This characteristic is quite dependent upon the prevailing cultural practices, and growing conditions, and therefore this is not a particularly distinctive characteristic of the new variety.

*Fruit form*.—Generally — Considered globose. The fruit is considered very uniform in its symmetry.

*Mucron tip*.—Absent.

*Fruit suture*.—No stitching exists along the suture line.

*Suture*.—Color — Generally, the fruit appears blushed to the same degree as the skin, (approximately RHS Orange-Red Group 34 A).

*Ventral surface*.—Form — Considered even, and uniform in appearance, when it is viewed from the lateral, sutural plane.

*Apex*.—Shape — Rounded, to slightly rutuse.

*Base*.—Shape — Generally gently retuse.

*Stem cavity*.—Generally — It extends in a rounded circular form which is generally considered uniform. The stem cavity is rounded but slightly extends toward the suture. The average depth of the stem cavity is about 8.0-10.0 mm. The average width of the stem cavity is about 26.0 mm. The average length of the stem cavity, when measured in the suturial plane is about 45.0 mm.

*Fruit skin*.—Thickness. — Considered medium in thickness, and tenacious to the flesh. Surface Texture. — Glabrous. Taste. — Non-astringent. Tendency to crack. — Not observed in the previous years of observation and evaluation.

*Fruit skin color*.—Blush Color. — Generally speaking, a red blush exists on a majority of the skin of the fruit (approximately RHS Red Group 45 A), and is more typically present on the portions of the fruit facing the sunlight. The blush of the fruit typically covers approximately 75%-95% of the fruit skin surface. The percentage of the blush on the fruit skin surface can vary, and is generally dependent upon the influences of the current season, and the fruit's exposure to direct sunlight; specific fruit maturity; and also the prevailing ecological and cultural conditions under which the fruit was grown.

*Ground color*.—A medium light-orange yellow, (approximately RHS Yellow-Orange Group 17 C). The ground color of the fruit can vary significantly based upon the maturity of the fruit when this measurement is taken, and generally gains a lighter, and less green cast with increasing maturity.

*Fruit glossiness*.—The fruit is considered to have a medium glossiness.

*Fruit stem*.—Size. — Medium in length, approximately 6.0 to about 8.0 millimeters. Diameter. — Approximately 2.0 to about 3.0 millimeters. Color. — Pale yellow-green, (approximately RHS Yellow-Green Group N144 C).

*Fruit flesh*.—Ripening. — Considered even. Texture. — Firm, crunchy, juicy and dense. The flesh is considered firm-melting. Lenticles. — Very weakly expressed. Fibers. — Present, but not prominent. Aroma. — Slight. Eating Quality. — Considered very good. Flavor. — Considered balanced with sweetness and acidity. Juice Production. — Moderate. Brix. — About 11.5 to 15.5 degrees. This characteristic varies slightly with the number of fruit per tree; the maturity of fruit when harvested; the prevailing cultural practices; and the ambient climatic conditions. Acidity. — Considered low. Approximately 0.8 titratible acidity. The acid levels assayed from fruit flesh can vary with fruit maturity, sunlight exposure, climatic, and other regional and cultural influences. Flesh Color. — It is considered yellow, (approximately RHS Yellow-Orange Group 17 D). A slight pigmentation of pink-red can be seen radiating from the stone (approximately RHS Red Group 39 A).

Stone:

*Type*.—Considered a clingstone.

*Size*.—It is generally considered to be medium for the species. The stone size can vary significantly depending upon the tree vigor, the crop load, and the prevailing growing and cultural conditions under which the tree was grown.

*Length*.—Average, about 30.0 to about 35.0 millimeters.

*Width*.—Average, about 23.0 to about 27.0 millimeters.

*Diameter*.—Average, about 17.0 to about 20.0 millimeters.

*Form*.—Roughly ovoid.

*Stone base*.—Shape — The stone is considered shortly attenuate.

*Apex*.—Shape — The stone exhibits a slight acute apex.

*Stone surface*.—Surface Texture — Considered irregularly furrowed toward the apex. Further, more pitting exists in the mid-portion of the stone (laterally), and is more common toward the base. Ridges. — Ridging is generally more prominent, and is usually oriented parallel, and laterally relative at the ventral and dorsal margins. Ventral Edge. — The ventral edge is generally described as having adjoining ridges formed from each hemisphere. There are longitudinal grooves running alongside this joined ventral suture. Secondarily, there can exist an additional set of parallel ridges, on each side of the major ridge. These secondary ridges are less prominent, and do not always extend from the hilum to the apex. Dorsal Edge. — Shape — Generally considered even. The folds of the surface ridges appearing on the external margins often end gently along the suture.

*Stone color*.—The color of a mature, dry stone is generally considered a dull brown, approximately (RHS Greyed-Orange Group 165 D). The stone color can vary considerably in view of how recently the fruit has ripened, the degree of oxidation which has taken place, and any blanching which has occurred due to the exposure of the stone to sunlight.

*Tendency to split*.—Splitting has rarely been noted.

*Kernel*.—Length. — Approximately 16.0-19.0 millimeters. Width. — Approximately 12.0-15.0 millimeters. Thickness. — 4.0-6.0 millimeters. Size. — The kernel is considered medium in size. Kernel Form. — Considered generally ovoid. Kernel Surface Texture. — The kernel pellicle is shortly pubescent. Kernel Color. — A dark tan (RHS Greyed-Orange Group 165 C).

*Use*.—The present variety 'Burnectthirtythree' is considered to be a nectarine tree of the late season of maturity, and which produces fruit which are considered to be firm, attractively colored, and which are useful for both local and long distance shipping.

*Keeping quality*.—Appears excellent. The fruit of the present variety has stored well for periods of up to 35 days after harvest at 1.0 degree Celsius.

*Shipping quality*.—Good. The fruit of the new nectarine tree variety showed minimal bruising of the flesh or skin damage after being subjected to normal harvesting and packing procedures.

*Resistance to insects and disease*.—No particular susceptibilities were noted. The present variety has not been intentionally tested to expose or detect any susceptibilities or resistances to any known plant, fruit diseases, insect, frost, winter injury or other environmental factors. Although the new variety of nectarine tree possesses the described characteristics when grown under the ecological conditions prevailing near Fowler, Calif., in the central part of the San Joaquin Valley of California, it should be understood that variations of the usual magnitude, and characteristics incident to changes in growing conditions, fertilization, nutrition, pruning, pest control, frost, climatic variables and changes in horticultural management practices are to be expected.

Having thus described and illustrated our new variety of nectarine tree, what we claim is new, and desire to secure by plant Letters Patent is:

1. A new distinct variety of nectarine tree, substantially as illustrated and described, and which is characterized principally as to novelty by producing an attractively colored, yellow-fleshed, clingstone nectarine which is mature for harvesting and shipment approximately July 30 to August 5 under the ecological conditions prevailing in the San Joaquin Valley of central California.

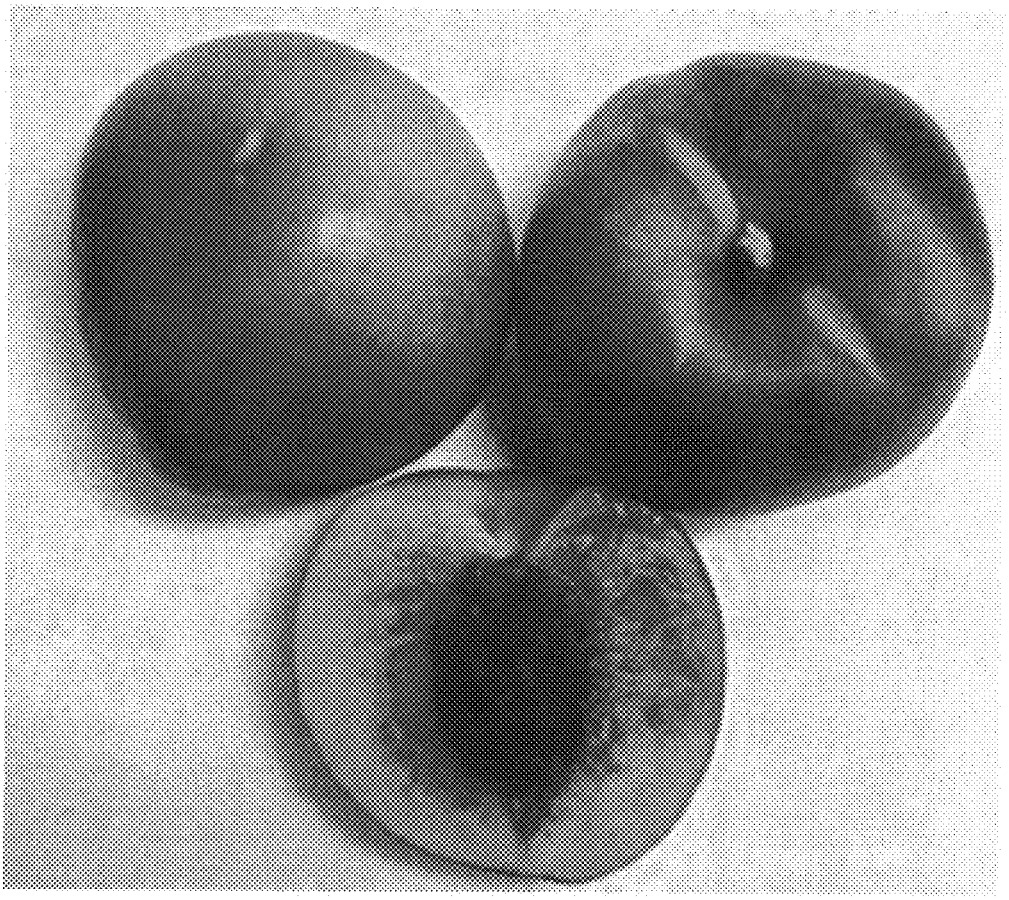

* * * * *